(12) United States Patent
McClellan

(10) Patent No.: US 8,187,203 B2
(45) Date of Patent: May 29, 2012

(54) BIOPSY NEEDLE SYSTEM, BIOPSY NEEDLE AND METHOD FOR OBTAINING A TISSUE BIOPSY SPECIMEN

(76) Inventor: W. Thomas McClellan, Fort Lauderdale, FL (US)

( * ) Notice: Subject to any disclaimer, the term of this patent is extended or adjusted under 35 U.S.C. 154(b) by 226 days.

(21) Appl. No.: 11/361,422

(22) Filed: Feb. 24, 2006

(65) Prior Publication Data

US 2007/0213633 A1     Sep. 13, 2007

(51) Int. Cl.
*A61B 10/00* (2006.01)
(52) U.S. Cl. .................. 600/567; 600/562; 600/564
(58) Field of Classification Search .......... 600/562, 600/564–567, 300; 606/167, 170
See application file for complete search history.

(56) References Cited

U.S. PATENT DOCUMENTS

| | | | |
|---|---|---|---|
| 4,236,273 A | 12/1980 | McCaffrey | |
| 4,619,304 A | 10/1986 | Smith | |
| 4,651,751 A | 3/1987 | Swendson et al. | |
| 4,651,752 A * | 3/1987 | Fuerst | 600/567 |
| 4,660,418 A | 4/1987 | Greenwood et al. | |
| 4,781,202 A * | 11/1988 | Janese | 600/567 |
| 4,897,081 A | 1/1990 | Poirier et al. | |
| 4,926,877 A * | 5/1990 | Bookwalter | 600/567 |
| 4,927,827 A | 5/1990 | Katoh et al. | |
| 5,007,532 A * | 4/1991 | Binish | 296/97.1 |
| 5,059,186 A | 10/1991 | Yamamoto et al. | |
| 5,127,537 A * | 7/1992 | Graham | 422/102 |
| 5,368,574 A | 11/1994 | Antonacci et al. | |
| 5,462,062 A * | 10/1995 | Rubinstein et al. | 600/567 |
| 5,626,597 A | 5/1997 | Urban et al. | |
| 5,827,305 A * | 10/1998 | Gordon | 606/159 |
| 5,885,226 A | 3/1999 | Rubinstein et al. | |
| 6,110,128 A | 8/2000 | Andelin et al. | |
| 6,355,335 B1 | 3/2002 | Kulkaski | |
| 6,709,408 B2 * | 3/2004 | Fisher | 600/570 |
| 6,827,692 B2 * | 12/2004 | Castellacci | 600/567 |
| 2002/0151821 A1 | 10/2002 | Castellacci | |
| 2005/0222520 A1 | 10/2005 | Faciszewski | |

OTHER PUBLICATIONS

International Search Report and Written Opinion dated Nov. 3, 2008.

* cited by examiner

*Primary Examiner* — Jeffrey G Hoekstra
(74) *Attorney, Agent, or Firm* — Laurence A. Greenberg; Werner H. Stemer; Ralph E. Locher

(57) ABSTRACT

A biopsy needle system includes a carrier. A trocar is inserted into the carrier for percutaneous insertion to a biopsy site. A biopsy needle is inserted into the carrier, replacing the trocar, for removal of a tissue biopsy specimen. A biopsy needle and a method for obtaining a tissue biopsy specimen with the system, are also provided.

15 Claims, 12 Drawing Sheets

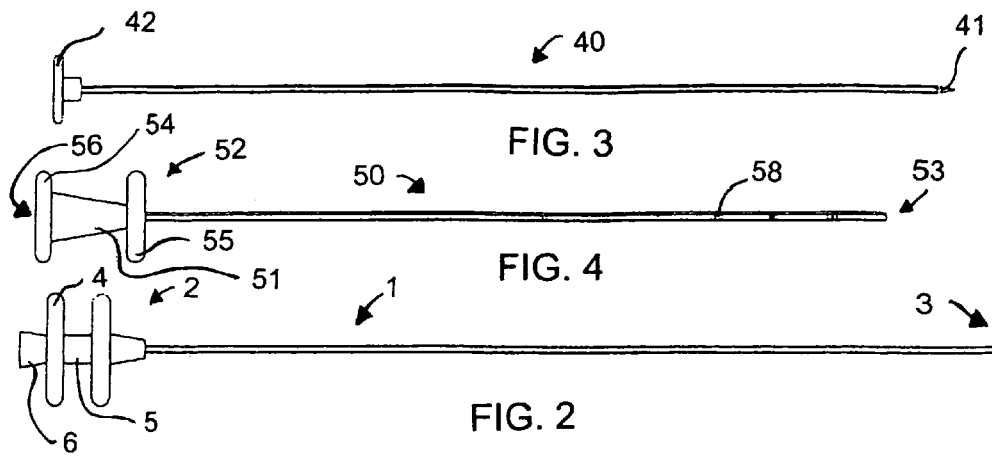
FIG. 3
FIG. 4
FIG. 2
FIG. 6
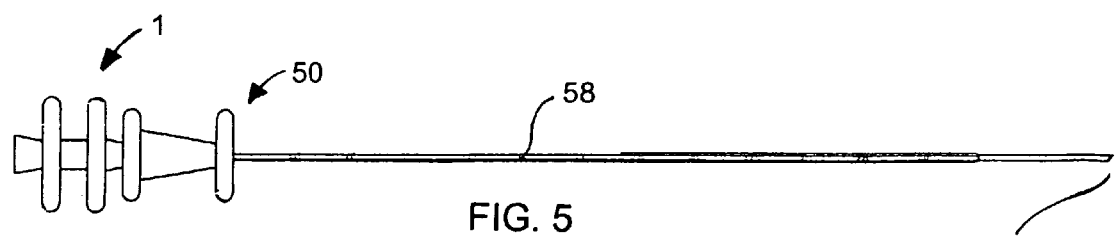
FIG. 5
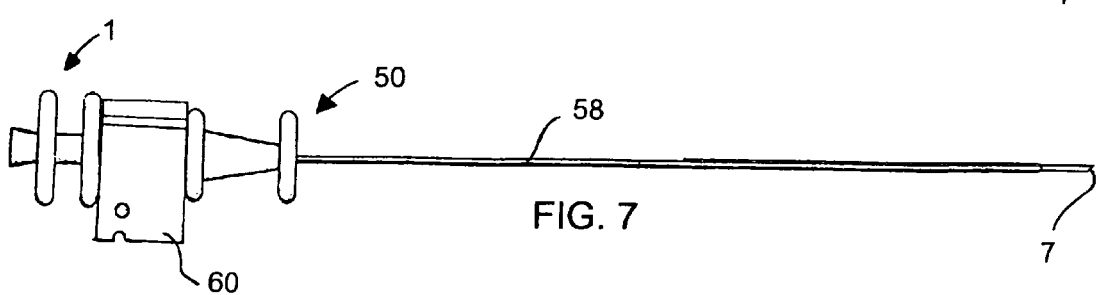
FIG. 7

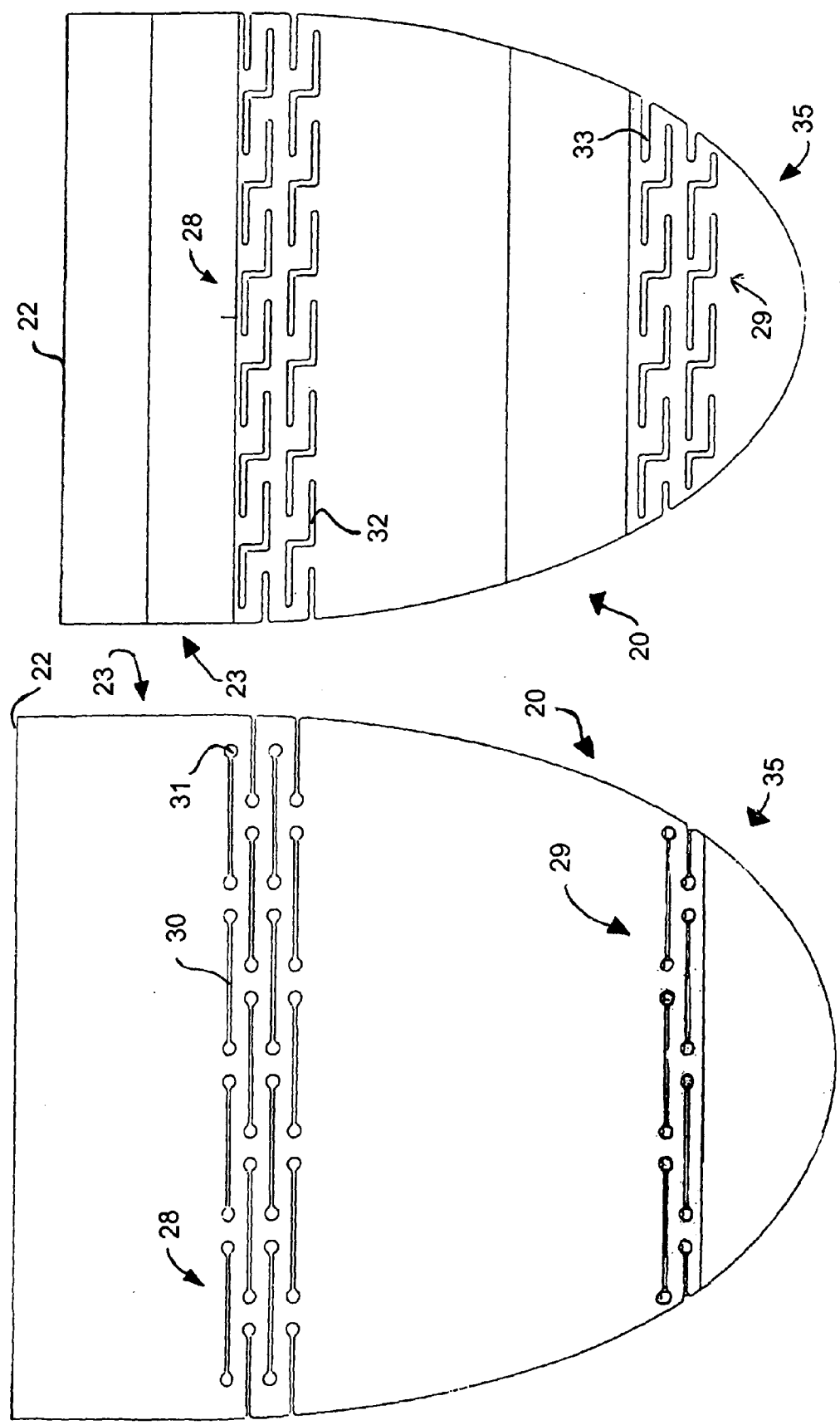

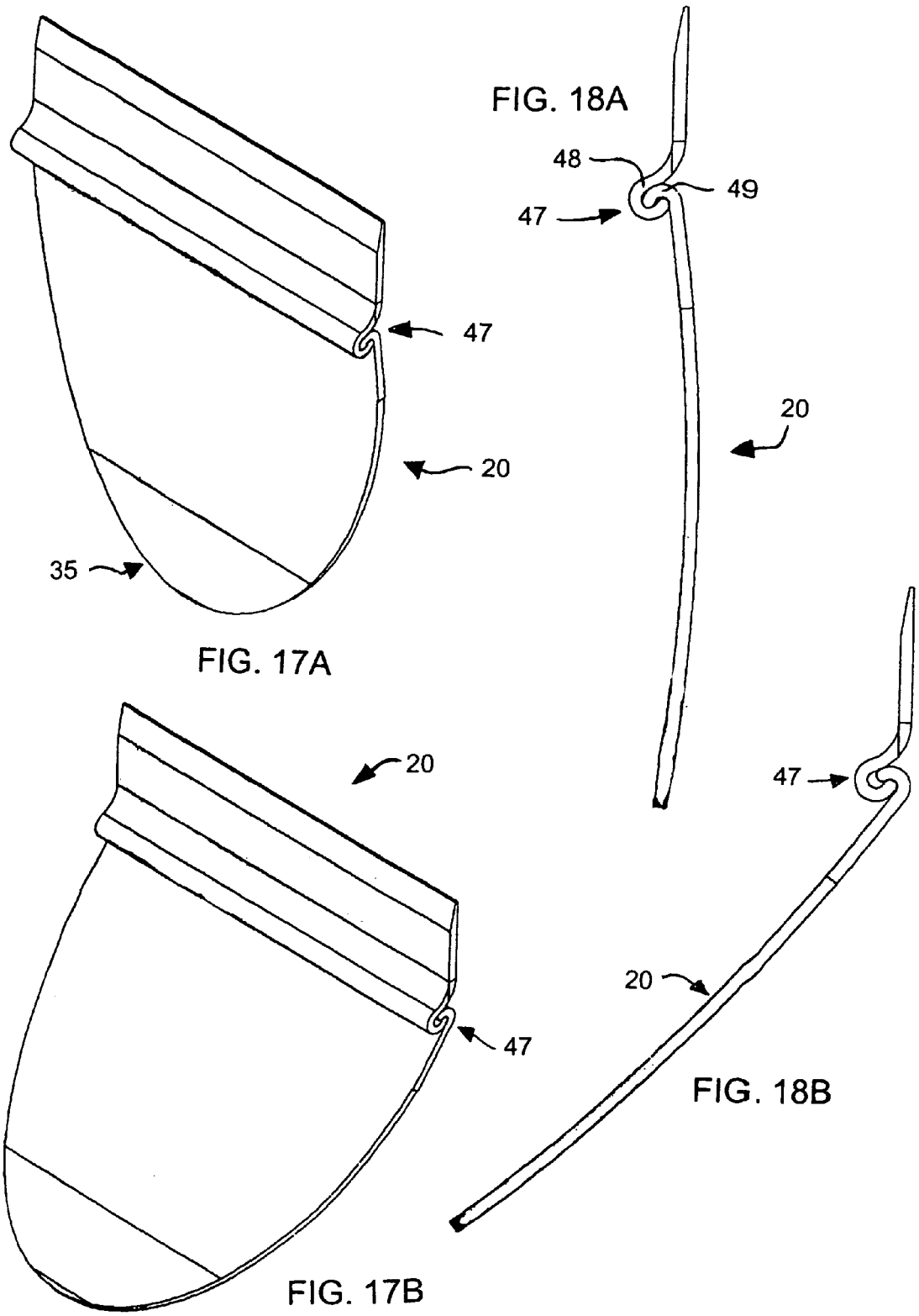

BIOPSY NEEDLE SYSTEM, BIOPSY NEEDLE AND METHOD FOR OBTAINING A TISSUE BIOPSY SPECIMEN

BACKGROUND OF THE INVENTION

1. Field of the Invention

The invention relates to a biopsy needle system, a biopsy needle and a method for obtaining a tissue biopsy specimen with the system.

2. Description of the Related Art

The most critical diagnosis in medicine is the presence or absence of malignancy. Although there are many screening tests: patient awareness, physical exams, blood tests, and new imaging systems, the hallmark of the cancer diagnosis is a physical specimen, or biopsy, for microscopic analysis.

Malignancy is of life or death importance, so that the quality of the biopsy is of utmost importance. Open surgical biopsy, with total control of specimen location, size, and condition, is the accepted standard of diagnostic quality and a minimally invasive, percutaneous or endoscopic biopsy must not sacrifice that quality, since a false negative may condemn the patient to an agonizing and preventable death.

Obtaining tissue is more difficult by any remote biopsy technique, but quality still relies on obtaining tissue of and from the suspected mass. Therefore, location of needle placement, tissue coring and preserving of the biopsy specimen are of critical importance.

New imaging systems improve needle placement, but with prior art biopsy needles, the actual capture of the biopsy specimen remains unsure and partially blind. The complex multi-motion sequencing of the typical side-cut biopsy needle is so demanding on operator skill, that even automation has not made it totally reliable.

A simple, one-motion, true end-cutting, core biopsy needle, which cleanly and safely shear-cuts straight ahead from the initial approach positioning, yet not blindly, would be an advancement in the art.

Endoscopic biopsy graspers and percutaneous biopsy needles generally recover limited, thin, short, slivers of tissue, making microscopic analysis and diagnosis difficult. An end-cutting, core biopsy needle, which recovers full-lumen specimens of almost unlimited length, would be an advancement in the art.

With the prior art, the biopsied tissue is frequently ripped, compressed, distorted or even crushed, limiting analysis and diagnosis. Fine needle aspiration biopsy, where the tissue is intentionally ripped into small segments or even single cell clusters, is so destructive to intracellular and intercellular anatomy that it is unwise to use that technique as any more than a screening test. Their cytology debris fields are of such poor condition, that although they can occasionally include the diagnosis of malignancy, they seldom exclude it.

An end-cutting, core biopsy needle that is totally non-traumatic to tissue and preserves intracellular and intercellular anatomy would be an advancement in the art.

SUMMARY OF THE INVENTION

It is accordingly an object of the invention to provide a biopsy needle system, a biopsy needle and a method for obtaining a tissue biopsy specimen, which overcome the hereinafore-mentioned disadvantages of the heretofore-known devices and methods of this general type, which are minimally-invasive, percutaneous or endoscopic and which not only exceed the prior art, but more importantly match the quality of an open surgical biopsy. The system, needle and method should be simple to use, easy to insert and control, reliable, safe, biopsy-depth adjustable, straight-ahead shearing, end-cutting, automatic-capture, longer full-lumen specimen, tissue-preserving, and over all a core biopsy needle system, a biopsy needle and a method for percutaneous and endoscopic use that improve biopsy quality.

With the foregoing and other objects in view there is provided, in accordance with the invention, a biopsy needle system. The system comprises a carrier, a trocar to be inserted into the carrier for percutaneous insertion to a biopsy site and a biopsy needle to be inserted into the carrier, replacing the trocar, for removal of a tissue biopsy specimen. The trocar and the biopsy needle are longer than the carrier, permitting a distal end of the trocar or the biopsy needle to extend beyond a distal end of the carrier. The system uses the trocar to strengthen the carrier upon initial insertion and relocation of the carrier and permits the needle to be inserted at the correct location and for cutting of the specimen only.

In accordance with another feature of the invention, the biopsy needle has a distal end with a cross-sectional shape having a flat side and a converging side. The converging side has a-semicircular, elliptical, oval, rounded, trapezoidal, paraboloid or triangular shape, although other shapes are possible as well.

In accordance with a further feature of the invention, the biopsy needle has a distal end, a lumen and a door disposed within the lumen at the distal end. The door is moveable freely about a hinge location from a normally open position lying at least partially against the flat side during percutaneous insertion, to a rotated and closed position contacting the converging side occluding the lumen and capturing the tissue biopsy specimen. The door has a fixed portion with a forward edge tapered and sharpened to decrease tissue passage entrance resistance. The door has a door tip opposite the hinge location for contacting the converging side and occluding the lumen. The tip is tapered and sharpened on a side facing away from the lumen and is turned down or angled toward a center of the lumen. The tip of the door is angled into the lumen to catch and dig into the tissue biopsy specimen upon retraction of the biopsy needle. Thus, an automatic door for catching and removing a tissue biopsy specimen is provided, which requires no other operation or manipulation other than advancement and retraction.

In accordance with an added feature of the invention, the biopsy needle has a distal end with a tissue cutting entrance, which is preferably angled relative to a longitudinal axis of the biopsy-needle. The tissue cutting entrance advances into the tissue biopsy specimen permitting the core to contact the door.

In accordance with an additional feature of the invention, there is provided a hinge interconnecting the flat side and the door at the hinge location. The hinge may be an articulating hinge, a tension-compression or live one-piece functional hinge, or a torsion element live or one-piece functional hinge. The hinge permits the door to swing away ahead of the specimen core and close behind it to obtain a tissue biopsy specimen.

In accordance with yet another feature of the invention, the door has at least one and preferably two flexing areas functioning as a hinge, which may be formed by cutting into the door, in particular in a pattern of separation lines. The flexing areas preferably each extend perpendicularly to the longitudinal direction of the door. This provides great flexibility of the door without an articulating hinge.

In accordance with yet a further feature of the invention, the door tip is angled into the lumen at one of the flexing areas closest to the door tip and is tapered and sharpened on a side facing away from the lumen, to catch and dig into the tissue biopsy specimen upon retraction of the biopsy needle.

In accordance with yet an added feature of the invention, the trocar has a tapered point protruding from the carrier.

In accordance with yet an additional feature of the invention, the trocar and the carrier have distal ends with cross-sectional shapes matching the cross-sectional shape of the biopsy needle. The most suitable of the above-mentioned cross-sectional shapes can be used for all three devices, the trocar, the carrier and the biopsy needle.

In accordance with again another feature of the invention, the carrier, the biopsy needle and the trocar each have at least one control ring. The carrier has a proximal end with a conically shaped or tapered entrance facilitating introduction of the biopsy needle and the trocar into the carrier. The control rings and the conical or tapered entrance facilitate operation and manipulation by an operator.

In accordance with again a further feature of the invention, the carrier has an outer surface with etched markings of insertion length. The markings aid in percutaneous insertion placement.

In accordance with again an added feature of the invention, there is provided a controller to be fitted on the biopsy needle, after insertion of the biopsy needle into the carrier, for adjustably gauging biopsy depth. The controller has a multiplicity of fitting regions each permitting a different biopsy depth. The controller is block-shaped and the fitting regions are slots or holes formed in the block-shaped controller having different lengths. The controller provides a simple way of adjusting cutting depth, with the longest depth being without use of the controller and decreasing depths being provided through use of the different fitting regions.

In accordance with again an additional feature of the invention, there is provided a syringe to be locked to the biopsy needle, after insertion of the biopsy needle into the carrier, for applying a vacuum to assist in tissue migration into the biopsy needle. The biopsy needle has a syringe connector, and the syringe has an end matching the syringe connector. The syringe connector and the end of the syringe are tapered conically. The syringe has a syringe plunger to be pulled out and locked for applying the vacuum. The syringe has a syringe body with a lip or peak, and the plunger has notches to be locked on the lip or peak. The syringe may be preloaded with a fluid, such as saline, to fill the biopsy needle while evacuating air and facilitate formation of a vacuum seal upon insertion of the biopsy needle and extraction of the tissue biopsy specimen. The vacuum syringe aids in extraction of the specimen and allows the specimen to be removed without being disturbed by manual manipulation of the operator.

With the objects of the invention in view, there is also provided a biopsy needle. The biopsy needle comprises a lumen, and a door disposed at the lumen. The door is moveable freely about a hinge location from a normally open position during percutaneous insertion, to a rotated and closed position occluding the lumen and capturing a tissue biopsy specimen for removal. All of the features of the biopsy needle of the biopsy needle system can be used in the biopsy needle apart from the other features of the system. For example, the cross-sectional shapes, the tapered and sharpened forward edge and tip of the door, the tissue cutting entrance, the hinges and the flexing areas may all be used as well.

With the objects of the invention in view, there is additionally provided a method for obtaining a tissue biopsy specimen. The method comprises inserting a trocar into a carrier, inserting the carrier with the trocar percutaneously to a biopsy site, removing the trocar from the carrier, inserting a biopsy needle into the carrier, and removing the tissue biopsy specimen with the biopsy needle. This method is simple to use, accurate and obtains a quality specimen. The rotation of the door, the decrease in tissue passage entrance resistance with a tapered and sharpened forward edge of the door, the flexing of the door, the catching and digging into the tissue biopsy specimen with the door tip and the movement of the door within the cross-sectional shapes, are all part of the method of the invention.

Other features which are considered as characteristic for the invention are set forth in the appended claims.

Although the invention is illustrated and described herein as embodied in a biopsy needle system, a biopsy needle and a method for obtaining a tissue biopsy specimen, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 2 is a side-elevational view of a biopsy needle of the system according to the invention;

FIG. 3 is a side-elevational view of a trocar of the system according to the invention;

FIG. 4 is a side-elevational view of a carrier of the system according to the invention;

FIG. 5 is a side-elevational view of the biopsy needle inserted into the carrier;

FIG. 6 is a side-elevational view of the trocar inserted into the carrier;

FIG. 7 is a side-elevational view of the biopsy needle inserted into the carrier, with a depth controller therebetween;

FIGS. 13 and 14 are views similar to FIG. 12 of the rotating door with two flexing areas;

FIGS. 17A and 18A are respective perspective and side-elevational views of the rotating door having an articulating hinge in a non-rotated position;

FIGS. 17B and 18B are respective perspective and side-elevational views of the rotating door having the articulating hinge in a rotated position;

DESCRIPTION OF THE PREFERRED EMBODIMENTS

Figure 1:
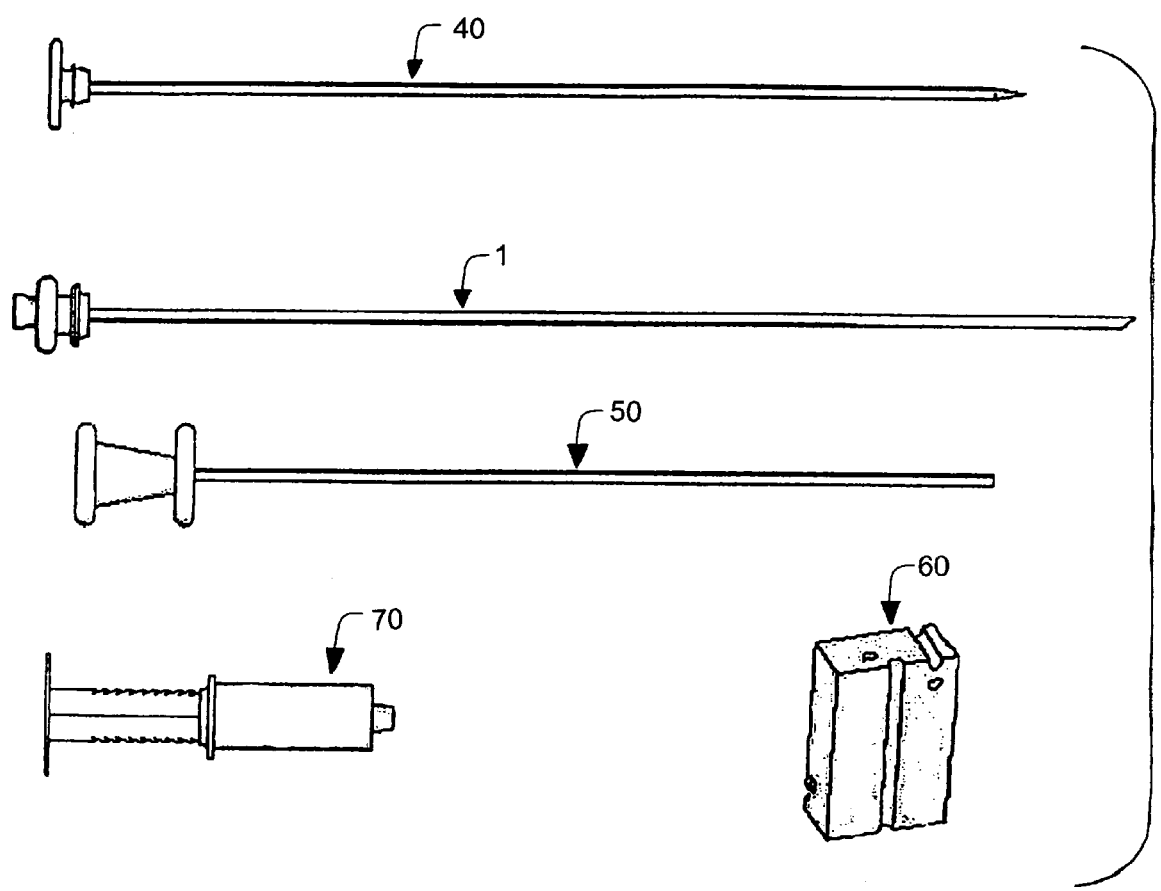
FIG. 1 is a diagrammatic, partially elevational and partially perspective view of a biopsy needle system according to the invention.

Referring now to the figures of the drawings in detail and first, particularly, to FIG. 1 thereof, there is seen a biopsy needle system according to the invention which has a biopsy needle 1, a trocar 40, a carrier 50, a controller 60 and a syringe 70. More specifically, the five-piece system includes:
  a. an integrated, reliable, true end-cutting, full-lumen specimen, coring, biopsy needle 1;
  b. an integrated, easy-insertion, biopsy needle carrier trocar 40;
  c. an integrated, improved-placement, high-reflectance, easy-insertion, biopsy needle carrier 50;
  d. an integrated, single-piece, dual-use, adjustable biopsy depth gauge and depth controller 60; and
  e. an integrated, dual-use, lockable, vacuum-assisted, coring and non-traumatic specimen removal syringe 70.

As is seen in FIG. 2, the biopsy needle 1 is formed as a tube-like structure, constructed of metal or other suitable material with a proximal end 2 (at the left in the figure) toward the operator and a distal end 3 (at the right in the figure) toward the object tissue. The proximal end 2 has a permanently attached control ring 4 for operator control, mounted over a tapered reinforcing collar 5, which also includes an inline, full size lumen-matching syringe connector 6 continuous with the needle lumen. The lumen is defined as all of the space or the passage or channel within a tube. The distal end 3 has a sharpened double angled, shear cutting edge tissue entrance 7, formed or angled at approximately 45 degrees from a centerline or longitudinal axis 15 and is constructed for an improved straightforward, non-blind, core cutting and capture of a tissue biopsy. This structure of angled cutting surfaces creates a shearing edge, as opposed to a right angle or straight across edge, which has increased cutting resistance and crushes tissues of very firm or soft consistencies. The distal end 3 with the tissue entrance 7 will be described in more detail below with regard to FIGS. 9 and 10.

As is seen in FIGS. 11A-11E, the tissue entrance 7 of the biopsy needle 1 is constructed with unique cross-sectional shapes. These shapes all have one flat side or section 8 covering of approximately one third of the circumference of the tissue entrance 7 and opposing walls covering approximately two thirds of the remaining circumference and having symmetrical, constantly closing angle wall configurations from the flat side 8, to close the tube or needle 1.

Figure 11A:
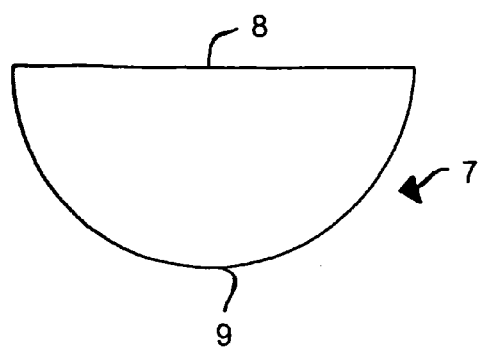
FIGS. 11A-11E are end-elevational views of the distal end of the biopsy needle showing different cross-sectional shapes.
Figure 11D:
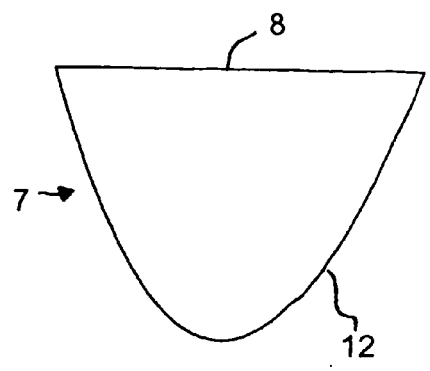
Figure 11C:
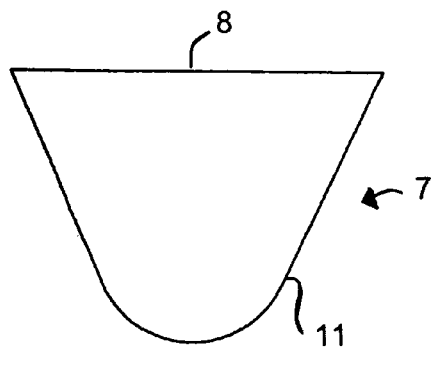
Figure 11B:
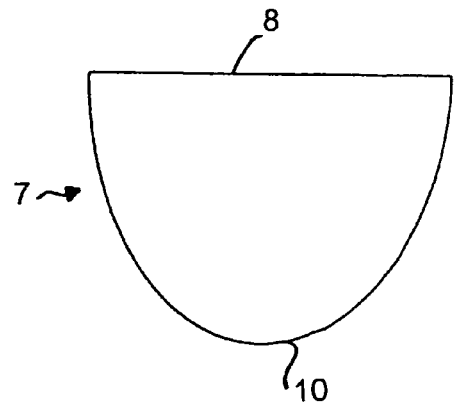
Figure 11E:
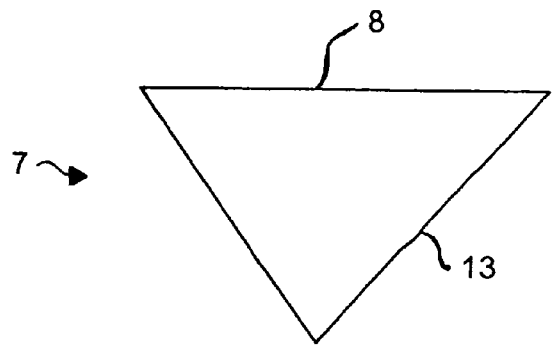

These opposing walls of the structural shapes, which are important to the invention, include a converging side 9 forming a semicircle in FIG. 11A, converging sides 10 forming an ellipse or oval in FIG. 11B, converging sides 11 forming a pure or rounded trapezoid in FIG. 11C, converging sides 12 forming a paraboloid in FIG. 11D, and symmetrical converging straight sides 13 forming a triangular shaped tube or needle in FIG. 11E.

Each of these shapes and similar ones with converging walls are used in the invention depending on needle type, intended use, length, size, operator preference, tissue type and tissue consistency. As will be explained below with regard to a door 20 of the invention, the converging wall shapes shown in FIGS. 11A-11E allow for continuous and simultaneous door to lumen wall occlusion, door rotation stoppage, complete tissue severing, uniform door edge support and reliable specimen capture.

Figure 9:
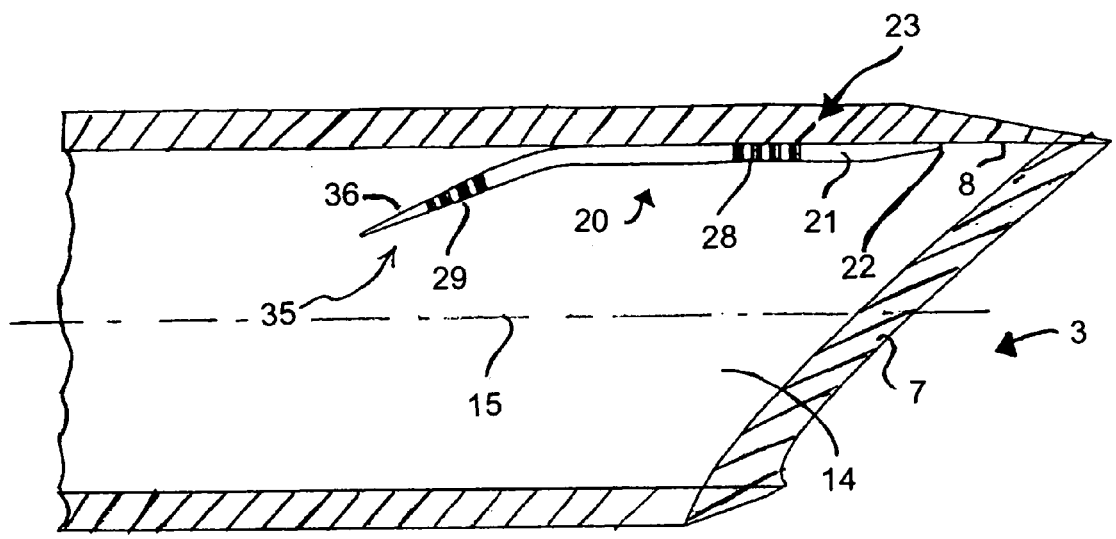
FIG. 9 is a fragmentary, greatly enlarged, cross-sectional view of a distal end of the biopsy needle with a rotating door in an open position.
Figure 10:
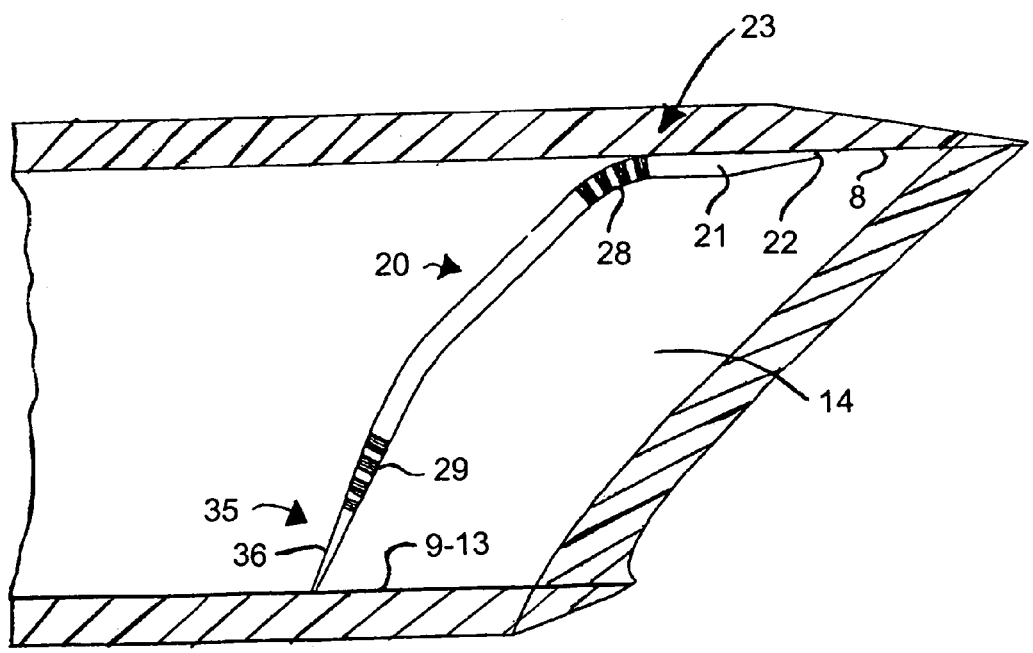
FIG. 10 is a view similar to FIG. 9 with the rotating door in a closed position.

The straight or flat side 8 provides a flat area for permanent attachment of a fixed half of a hinge to the rotating hinged door 20. This end-cutting door 20, which is located just inside the distal tissue entrance 7, as is seen in FIGS. 9 and 10, is the part of the invention which allows for automatic end cutting of the needle biopsy core specimen.

A fixed or nonmoving portion 21 of the door 20 has a forward (lumen side) edge 22 which is tapered and sharpened to decrease tissue passage entrance resistance. The hinged door 20 moves freely about a hinge location 23 from its normally open position shown in FIG. 9 in which it lies against the straight wall or flat wall segment 8 during insertion, to an opposite extreme of being fully rotated and closed against the opposing wall or converging side 9-13 as is seen in FIG. 10, totally occluding the passageway or lumen 14 and capturing the biopsy tissue.

The hinged door 20 and the converging walls or sides 9-13 work in combination to form and function as the long sought after, true end-cutting biopsy needle. The constantly converging walls or sides 9-13 form a continuous and simultaneous shearing occlusion between the lumen 14 and the lumen-shaped door 20. This hinged door 20 is contoured to fit the lumen 14 perfectly at about a 35 to 45 degree arc segment of the needle lumen or on a line running approximately 35 to 45 degrees from a centerline of the lumen, as is seen in FIG. 10. The distal end 3 of the needle tube is formed at approximately a 40 to 50 degrees angle and the hinged door 20 stops or occludes at roughly 5 to 15 degrees of rotation short of the end of the needle. The door 20 intentionally impacts the opposing or converging lumen walls or sides 9-13 uniformly and is supported along the entire circumference, stopping and shearing, without any other operator action, mechanical parts or latches. Further door rotation or pass through failure is prevented.

This structure according to the invention has been developed because it has been found that with non-converging angle walls, such as with a square tube, there is no uniform contact or shearing, the door is unevenly supported, being held only at the hinge and opposite wall. The door flexes centrally, shortens, and over rotates, with pass through door failure and tissue specimen loss.

Three separate embodiments of hinge structures may used in the end-cutting door 20 according to the invention, depending on needle size, length, intended use, operator preference, tissue type and tissue consistency.

First is a macro-machined or formed, common articulating hinge 47 provided at the hinge location 23, where two or more pieces rotate 48, 49 in relation to each other at, around, or as, a joint. The joint is provided with a standard axle element and interlacing fingers, such as in a typical door or piano hinge, or one piece 48 may be in the shape of an eye and the other piece 49 may be in the shape of a hook, cooperating with each other, as is seen in FIGS. 17A, 17B, 18A and 18B. These hinges demonstrate high flexibility and a large range of motion, but have higher resistance to tissue passage into the lumen 14 because of their increased bulk. They are more difficult to manufacture economically, suffer more binding between the parts with a greater tendency toward failure to the hinge or even worse, hinge separation failure, than with the other embodiments.

Figure 12:
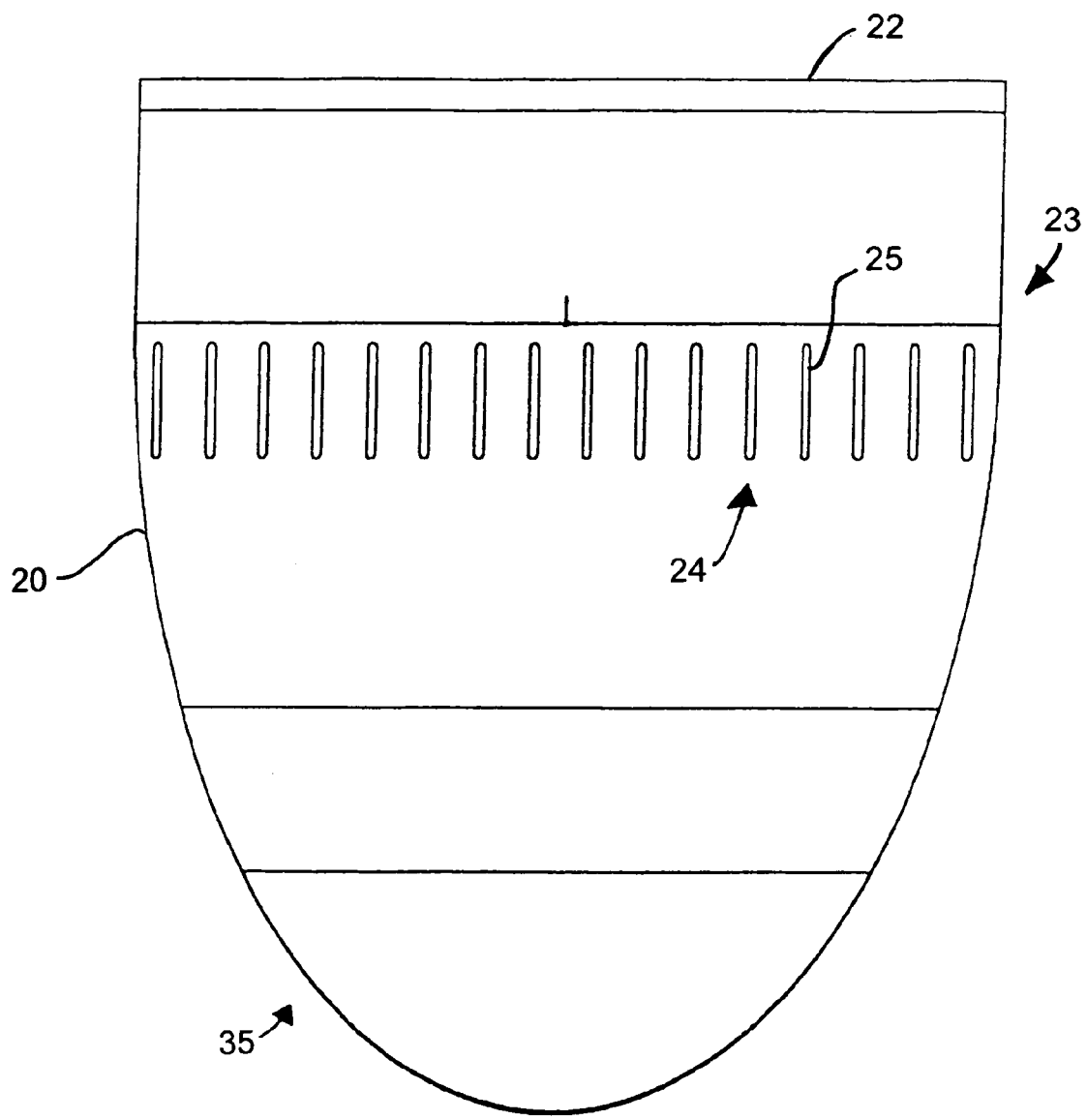
FIG. 12 is a further enlarged, front-elevational view of the rotating door with a flexing area.

Second is a micro-machined or formed, tension/compression live hinge where an area 24 of the door material itself flexes and becomes a functional hinge. This bending or flexing area 24 of door material may be thinned, narrowed, lengthened, or separated into two or more active hinge segments to improve flexibility of the bending area. The hinge element shaping or separation area 24 has lines 25 generally formed or cut at right or high angles of 45 to 90 degrees to a hinge or flexing axis as is seen in FIG. 12. Opposing, top and bottom surfaces of this live hinge structure are alternately placed in tension and compression. These functional hinges show higher initial strength with more limited flexibility, lower cycle tolerances and higher failure rates due to molecular strain and disruption in the area of tension, than the other embodiments. Lengthening or broadening the hinge area 24 improves flexibility but if the flexing area 24 is broadened in the hinge to tip dimension, the longer flexing area 24 causes the door length and fit to the lumen walls to change. More problems are experienced than with the other embodiments, especially with changes of tissue consistency, with unpredictable occlusion against the opposing wall with either premature or incomplete closure to over rotation and pass through of the intended support angle and door failure.

Figure 15:
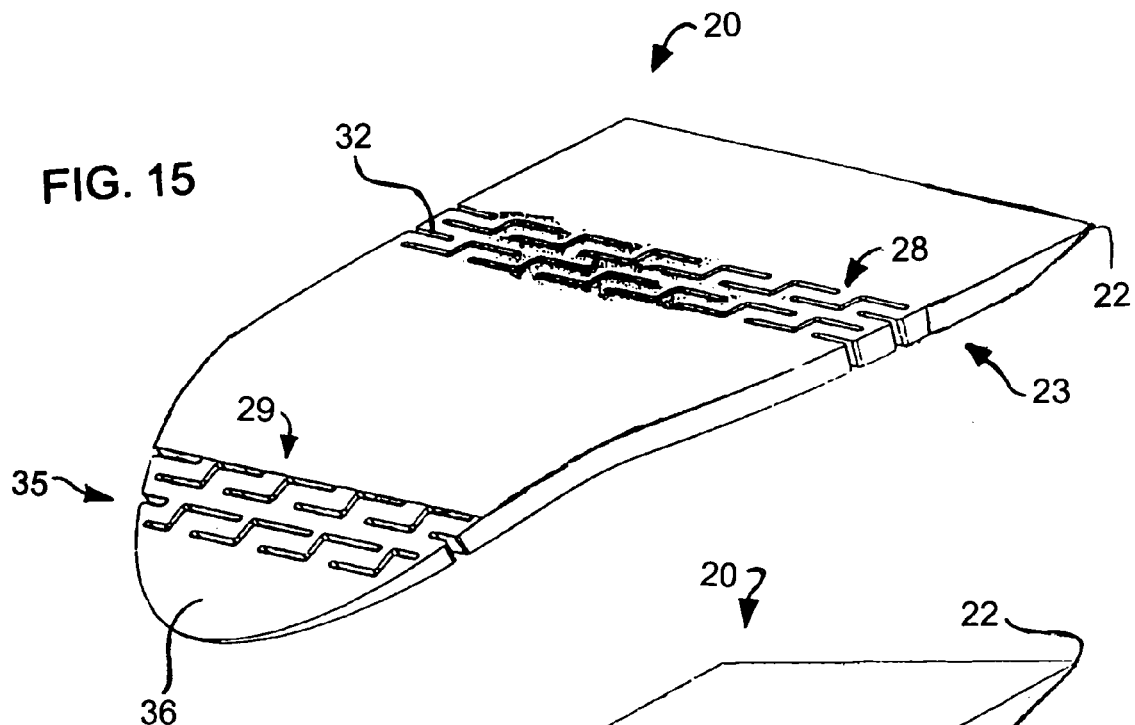
FIGS. 15 and 16 are perspective views of the rotating door with two flexing areas in different flexing positions.
Figure 16:
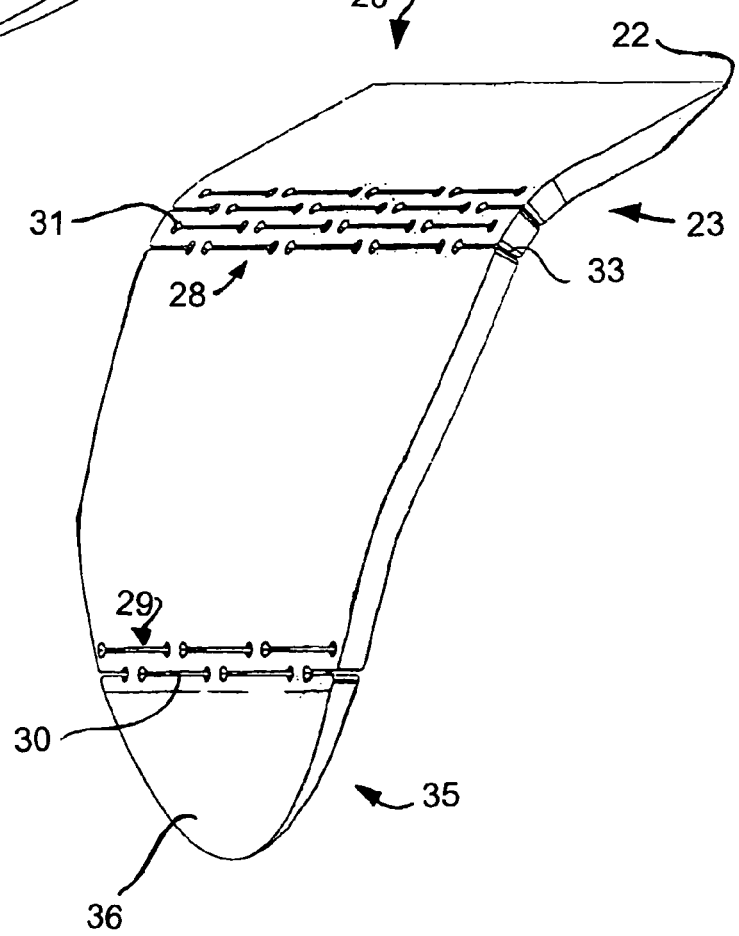

Third is a micro-machined or formed torsion live hinge where an area 28 of the door material itself flexes and becomes a functional hinge. This flexing area may be separated into two or more active hinge element areas 28, 29, generally by micro-machining or laser cutting, to improve flexibility, widen the flexing area, decrease molecular strain and improve reliability. The illustrated flexing areas extend perpendicularly to a longitudinal direction of the door, between the hinge location 23 and the tip 35. However, it is merely a manipulation of the angle, length, width, overlap and pattern, of the formed separations which converts the tension/compression areas into improved function, torsion areas. The hinge areas 28, 29 have separation lines 30, 32 that are formed or cut generally parallel to, or at low angles of 0 to 45 degrees to, the hinge or joint axis, as is seen in FIGS. 13, 14, 15 and 16. The lines 30 have holes 31 at the end for preventing tearing as is seen in FIGS. 13 and 16. The lines 32 shown in FIGS. 14 and 15 are generally S-shaped with angles of 90 degrees within the S and several straight segments 33 toward the periphery, so that most lines extend across a greater region in the direction from hinge to tip of the door 20 than the straight lines 30.

Opposing surfaces of these overlapping hinge areas 28, 29 are alternately placed in bi-directional or shared torsion, which not only has low molecular strain or disruption but also less flexing resistance. Narrowing, lengthening, or varying the overlap or shape of the individual torsion areas 28, 29 by the form or pattern of cuts of the lines 30, 32 or by adding additional torsion zones, can improve flexibility and further reduces molecular strain. This structure is functionally reliable, dimensionally stable, has high flexibility, high cycle capability, high strength, low heat build up, low molecular distortion and low failure rates. This hinge structure works well with a broad range of tissue types and consistencies.

Another important feature of the end-cutting door 20, is the structure of a distal door tip 35, opposite from the hinge location 23. This tip 35 is tapered and sharpened on the side 36 facing away from the distal end 3 of the lumen 14, and is turned down or angled toward the center of the lumen as is seen in FIGS. 15 and 16. The second or additional flexing area 29 facilitates the tip 35 to flex away from the inward passing tissue and also flex into the outwardly passing tissue. These four features are combined and adjusted to act as a catch or barb, to hook into the tissue specimen as the tissue attempts to reverse its movement in relation to the needle 1, when the biopsy needle 1 is moved rearward or away from the area of biopsy. The tissue plug or specimen, still being connected to its organ system, will be held by its own tissue cohesion and attempt to remain in place as the needle is withdrawn, with the tissue being pulled out of the needle 1 unless the door tip 35 intervenes.

This door tip 35 is constructed to be automatic in function. At insertion, the tip 35 allows the tissue to pass without restriction into the needle 1, but upon the first rearward movement of the tissue, the tip catches and digs into the tissue. Cutting into and across the specimen, which continues the further rotation of the door 20 until it strikes the opposing contour fitting or converging walls or sides 9-13 uniformly and simultaneously severing or end cutting and capturing the tissue core of biopsy specimen.

The biopsy specimen is now safely trapped within the lumen 14 and held by the automatic door 20 for easy and non-traumatic removal. Just the simple act of insertion cleanly shear-cuts or cores the specimen and just as simply withdrawal automatically hooks, end cuts, severs, and captures the biopsy specimen. The end-cutting door 20 is freely moveable within its controlled range and needs no separate activation by the operator or automation. The structure of the hinge location 23 and the digging-in movement of the turned down distal door tip 35 create all the door rotational forces.

The important structural elements of the biopsy needle include:

1. The biopsy needle 1 having an inline, full size lumen-matching syringe connector 6 at the proximal end 2, which is continuous with the needle lumen 14 for vacuum application and specimen removal and a tapered re-enforcement 5 for fitted engagement with the biopsy needle carrier 50.

2. The distal end 3 having a sharpened, double angled, shear cutting tissue entrance 7 formed at approximately 45 degrees from the centerline for straight forward, non-blind shearing of a core biopsy specimen.

3. The needle 1 being constructed of several functionally important structural cross-sectional shapes, with one side 8 being straight or flat and opposing walls being symmetrical, constantly closing angle or converging walls or sides 9-13 joining and forming the needle tube.

4. The distal end 3 having a hinged, end-cutting door 20, with a fixed, non-moving, hinge location 23 being permanently affixed to the flat side 8, and its tissue facing forward edge 22 being tapered and sharpened. The hinged door 20, rotating from its open or position of repose against the flat wall side 8, allowing the tissue into the lumen 14, to the closed position, against and occluding with, the opposing walls or sides 9-13, where the combination of the two complementary shaped surfaces come together to sever and capture the biopsy specimen.

5. The hinge structures include an articulating hinge, a tension-compression or live one-piece functional hinge and a torsion element live or one-piece functional hinge.

6. The tip 35 of the hinged door 20 being tapered and sharpened on the side 36 facing away from the distal end 3 of the lumen 14, coupled with the tip 35 of the door being angled into the lumen and with the additional hinging area 29 to catch and dig into the specimen on its rearward movement. By intention, this angled portion causing further rotation of the door 20 through and severing the specimen upon impaction and occlusion with the opposing walls or sides 9-13 and capturing of the specimen.

Figure 8:
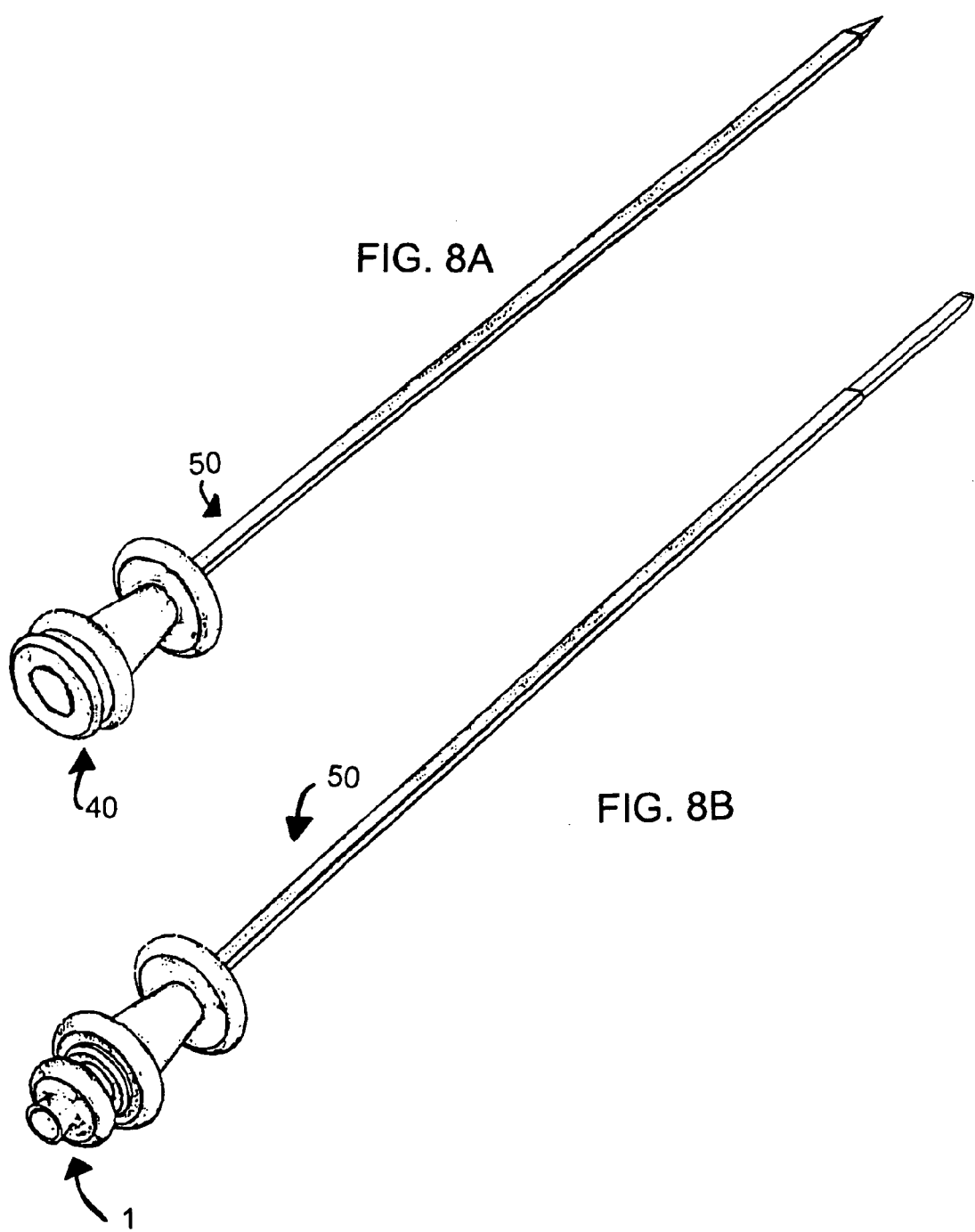
FIG. 8A is a perspective view of the trocar inserted into the carrier.
FIG. 8B is a perspective view of the biopsy needle inserted into the carrier.

The biopsy needle and trocar carrier 50 seen in FIG. 4 is a tube-like structure with a permanently attached reinforcing area 51 and double grasping control rings 54, 55 surrounding a proximal end 52, toward the operator, with a tapered entrance channel 56 to facilitate and protect the insertion of the trocar 40 or biopsy needle 1 into the positions shown in FIGS. 7 and 8, respectively. A distal end 53 has a right angle or straight across termination, which is tapered and has a sharpened edge around its entire circumference, to aid insertion into the subject tissue.

The biopsy needle carrier 50 is constructed of metal or other suitable material, in matching variations of lengths from 8 cm to 40 cm and in equivalent cross-sectional diameters of 10 to 18 gauge. The carrier 50 has cross-sectional shapes matching the biopsy needles 1 and trocars 40, but is slightly larger, since the carrier is constructed to fit snuggly over the biopsy needle as seen in FIG. 8B or over the trocar as seen in FIG. 8A, for ease of introduction through the body layers and to safely contain and support the biopsy needle 1 to the proper location and anglulation, for beginning the biopsy coring, done by the biopsy needle 1, through the carrier 50. The biopsy needle carrier 50 and the trocar tip 41 have a smooth contour for insertion and penetration of layers, as is seen in FIGS. 3, 4, 5, 6, 7, 8A and 8B.

The important structural features of the carrier 50 include:

1. The biopsy needle carrier 50 having a conically shaped or tapered entrance 56 to the lumen at the proximal end 52 for facilitating the introduction of the biopsy needle 1 and trocar 40 without abrasion, damage or dulling of their sharpened edges.

2. The biopsy needle carrier 50 matching the cross-sectional shapes of the biopsy needle 1 and trocar 40.

3. The biopsy needle carrier 50 being intentionally shorter than the biopsy needle 1 by four centimeters as is seen at the right side of FIGS. 5 and 8, providing for precise adjustability of biopsy depth in 1 centimeter increments, from 4 cm down to 1 cm in length.

4. The biopsy needle carrier 50 having tissue-penetrating smooth walls, seen in FIG. 4.

The biopsy needle carrier trocar 40 seen in FIG. 3 is configured and constructed of a suitable material to act as an insertion and strengthening aid for the biopsy needle carrier 50. In percutaneous biopsy, there are several layers of tissue which the biopsy system must pass through, in order to reach the biopsy site and since such relatively large bore needles cannot be made with cutting tips because of tissue damage, a tapered and pointed central lumen filler, or trocar 40 with a control ring 42, must be added to assist insertion.

The biopsy needle 1 is also relatively long and is maneuvered during insertion with bends and angle changes. These leverages or bending forces also require the stabilizing and strengthening of the needle carrier 50 with a full size strong trocar 40. The trocar 40 is constructed to fit snuggly within the lumen of the biopsy needle carrier 50, matching the carrier in size, cross-sectional shape and being slightly longer in length with a finely tapered point 41 that protrudes from the carrier 50 as is seen in FIGS. 3 and 6.

Insertion of the relatively large bore round object through multiple fibrous layers meets with an exaggerated resistance related to the phenomenon of pressure desiccation or drying and stretching by the compression of tissue layers ahead of the trocar 40 and carrier 50.

The forced advancement of the encased round trocar 40 drives the normal interstitial fluid from the contacting tissue and stretches the fibrous layers, creating a collapsing, tightening, fibrous tube surrounding the carrier 50 and trocar 40, much like a Chinese finger trap. This pronounced increase in resistance takes significant pressure to overcome, decreases the tactile feel or proprioceptive feedback to the operator and increases the risk of misplacement or break-through-over-insertion trauma to other organ systems.

The trocar 40 and carrier 50 are inserted and maneuvered as a single unit. Between biopsies, performed by the biopsy needle 1, the trocar 40 is reinserted within the carrier 50 for any repositioning or angle change of the carrier. The objective is to insert and maneuver the carrier 50 to the perfect depth and position, with the tip of the carrier just at the beginning of the planned biopsy tract and at the proper angle for insertion of the biopsy needle 1, with predictable, not blind, straight ahead core cutting of the tissue of interest. The biopsy needle carrier 50 is also constructed with etched markings 58 of insertion length, in centimeters, on its outer lateral surfaces for more precise placement, as is seen in FIGS. 4-7.

Figure 19A:
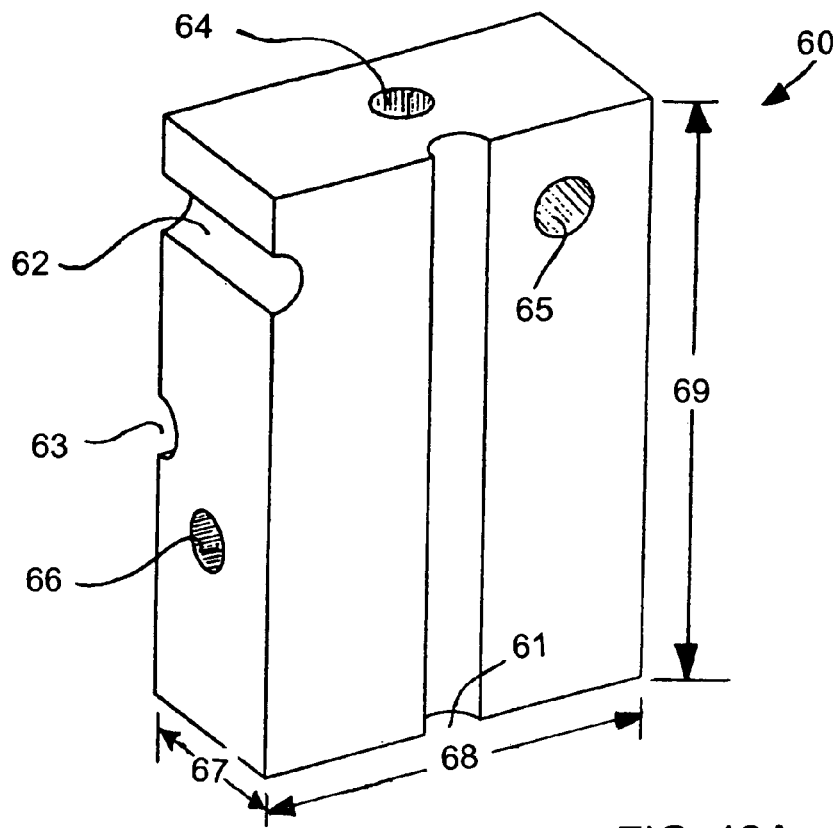
FIGS. 19A and 19B are enlarged, perspective views of a controller of the system according to the invention.
Figure 19B:
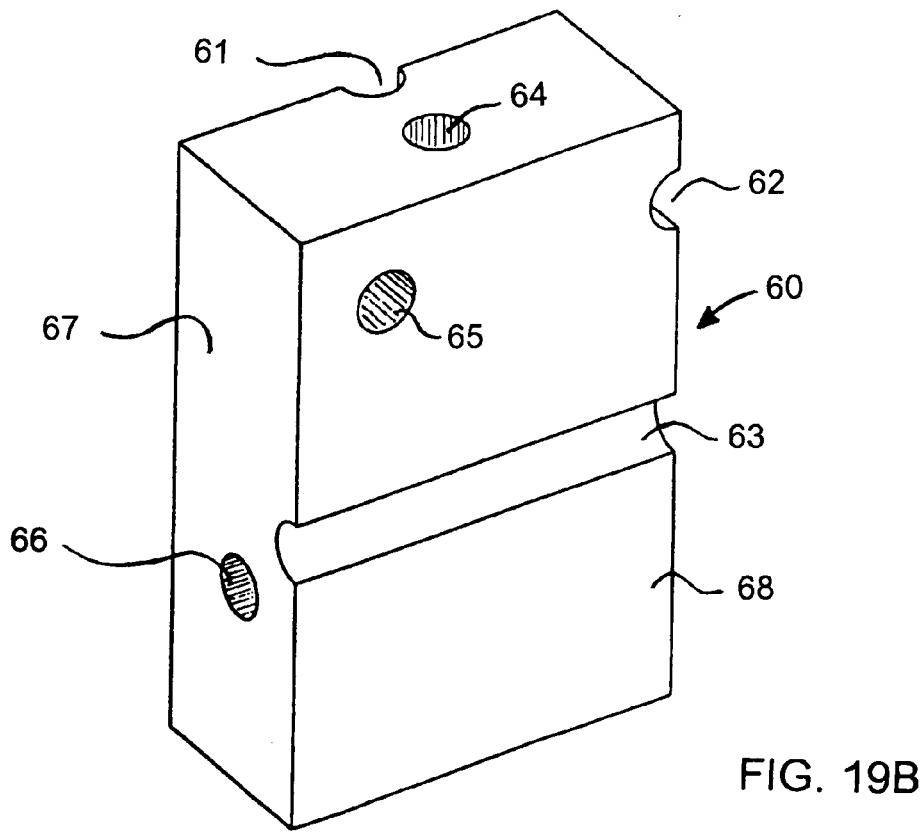

A single-piece, dual-use, four-separate-depth, adjustable biopsy depth gauge and depth controller 60 is shown in detail in FIGS. 19A and 19B. The controller is provided in recognition of the importance of having at the operators' option, a method to gauge and control the depth of the biopsy to protect contiguous organ systems. The carrier 50 is placed with great intention in proper position, relation, and angle to the target tissue and with the biopsy needle 1 being 4 cm longer than the carrier 50. Thus, a desirably safe, simple, easy to use, one-piece method to gauge and control the reach or depth of the biopsy needle 1 beyond the carrier 50 is presented.

The domino-shaped clip-on or slide-on controller 60 according to the invention, which contains three separate, measured, dual use sides, shown in FIGS. 19A and 19B, satisfies this requirement. The depth gauge and biopsy depth controller, configured with the dual-use system, includes a multiplicity of fitting regions, namely three self-grasping fitted slots 61, 62, 63 constructed for convenient snap-on, after needle insertion or changing depth use and three matching, fitted holes 64, 65, 66, for preplanned and more secure slide-on use. Without the controller 60, the extension beyond the carrier or biopsy coring will be 4 cm in depth, if clipped or fitted on the side with the shortest dimension 67, 3 cm in depth, if clipped or fitted on the side with the middle dimension 68, 2 cm in depth and if clipped or fitted on the side with the longest dimension 69, 1 cm in depth. The mounting of the controller 60 between the needle 1 and the carrier 50 can be seen in FIG. 7. The clip-on, slide-on gauge becomes a simple, effective and safe structure to gauge and control biopsy depth.

Figures 20A, 20B, 20C:
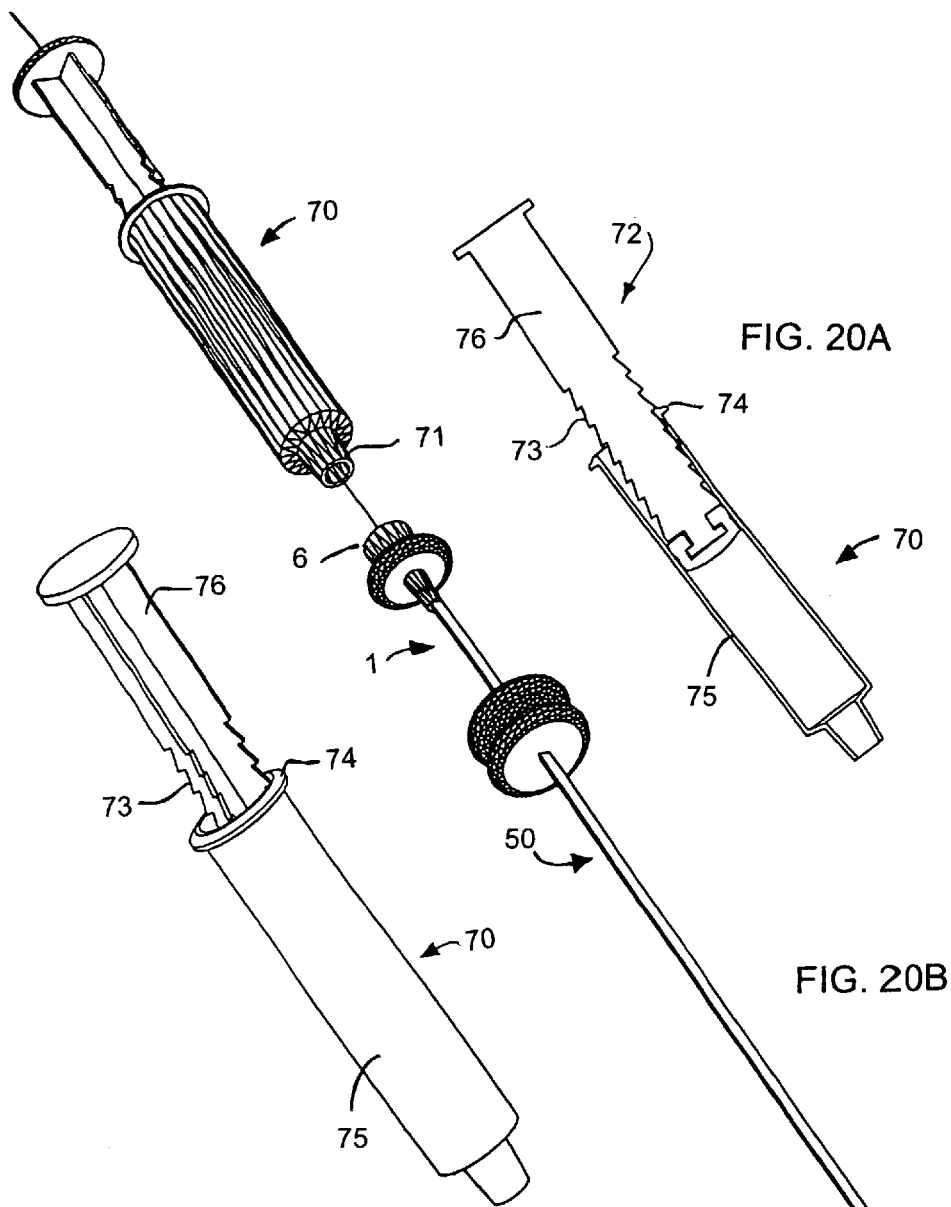
FIGS. 20A, 20B and 20C are enlarged, perspective views showing a syringe of the system according to the invention in three positions with and without the biopsy needle.
Figure 21A:
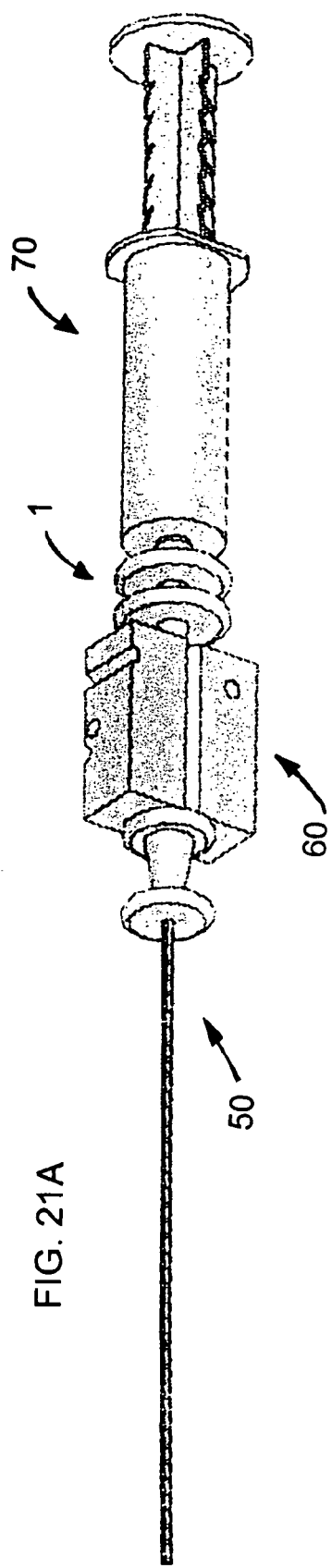
FIGS. 21A and 21B are side-elevational views of the assembled carrier, controller, biopsy needle and syringe, in two different positions of the controller.
Figure 21B:
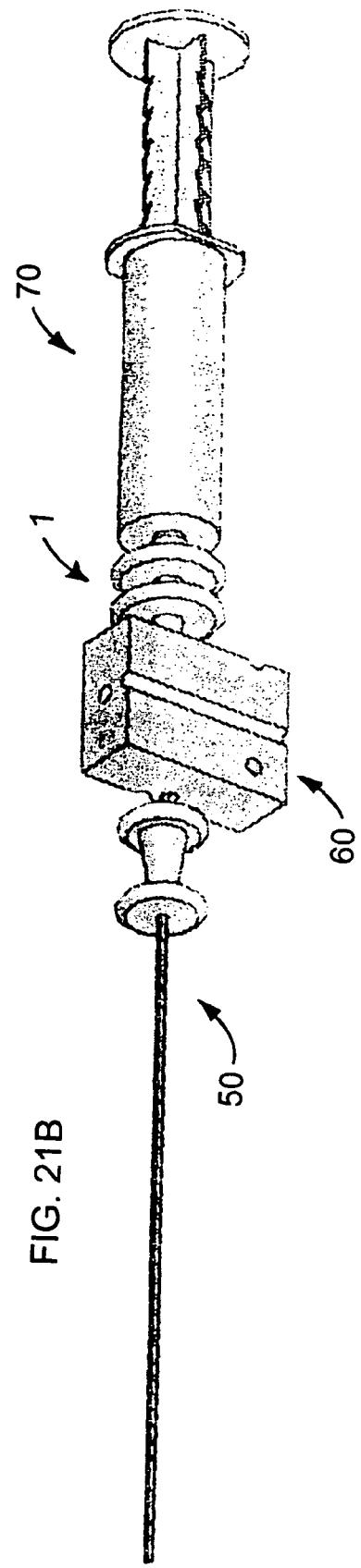

A lockable, vacuum-assisted, coring and non-traumatic specimen removal syringe 70 is shown in FIGS. 20A, 20B and 20C. The syringe provides the desirable option to the operator of a method for vacuum assisted biopsy coring. Tissues of extremely firm or soft consistencies are difficult to advance cleanly into a biopsy needle lumen and is the most common cause of biopsy recovery failure. The application of a continuous vacuum throughout the coring insertion pulls or assists the tissue migration into the needle lumen 14. Once the biopsy needle 1 is inserted through the carrier 50, and sealed against the target tissue, the lockable vacuum-pulling syringe 70 is attached to the biopsy needle syringe connector 6 using a larger-than-lumen, tapered and matching conically shaped end 71 as is seen in FIG. 20B, and the vacuum is applied by pulling out and locking a syringe plunger 72. Of course, the controller 60 may be disposed between the biopsy needle 1 and the carrier 50 in any of its positions, two of which are shown in FIGS. 21A and 21B, depending on the desired depth of penetration, as described above.

Another important structural feature of the locking syringe is interlocking counter-angled edges. The edges firstly include a narrow, upwardly-angled lip or peak 74 around the top of a syringe body or cylinder 75, and secondly downwardly-angled notches 73 formed in the lower third of four blade-shaped columns 76 of the plunger 72 of the syringe 70, three of which are seen in FIG. 20c. An operational feature is that the syringe comes preloaded with normal saline to fill the biopsy needle 1 while evacuating the air, to provide a more effective vacuum seal upon insertion and extraction of the specimen.

Once vacuum is applied, the plunger 72 is moved off center as is shown in FIG. 20A, engaging and locking the two counter-angled edges 73, 74, which are now held in the locked position by the force of the pre-selected vacuum. The biopsy needle 1 is then advanced with vacuum assisted coring of the biopsy specimen. The vacuum is automatically released upon withdrawal, with exposure to the atmosphere.

The dual-use ability comes from the large needle to syringe connector 6 and the residual vacuum of coring. Upon withdrawal, the atmospheric pressure automatically and non-traumatically pushes the cored specimen into the vacuum and specimen recovery syringe 70. The biopsy specimen, contained within the syringe, can then be released over an absorbent cloth by the operator and transferred with non-grasping instruments into the pathology container and preservative. The untouched biopsy specimen is maintained in perfect condition. The biopsy is completed and quality is assured.

The integrated, complete, and all-inclusive biopsy system is constructed for multidisciplinary use. Its availability in sizes (from 10 to 18 equivalent gauge) and lengths (from 8 cm to 40 cm) makes it suitable for many biopsy techniques and procedures. The hinge and needle shape variations, with the option of vacuum assistance, create a compatibility with many tissue consistencies or organ systems. Its increased reflectivity and visibility, compatible to new imaging technologies, yield a level of control, depth and angle precision not previously seen.

The invention provides a true end-cut tissue biopsy, equaling the qualities of an open surgical biopsy, but using a minimally invasive technique.

Improved, minimally invasive biopsies are now available for fields including, but not limited to, the following:
 a. unguided, percutaneous needle biopsy, as in obvious, palpable subsurface solid masses;
 b. manually or finger-guided, percutaneous biopsy, such as transrectal, or transperineal prostatic needle biopsy, etc.;
 c. visually-guided, open surgical needle biopsy with an exposed mass or tissue;
 d. visually-guided, trans-orifice biopsy such as oral, nasal, tracheal, or rectal needle biopsy, etc.;
 e. remotely or virtually-visualized, and guided percutaneous needle biopsies of internal organ systems, such as breast, lung, kidney or liver biopsy, etc.;
 f. endoscopically-guided, percutanous or trans-instrumental needle biopsy of internal organs such as bladder, prostate, bronchial, esophagus, sigmoid, etc.;
 g. laproscopically guided trans-abdominal, percutaneous or trans-instrumental, needle biopsy of internal organs, including ovary, bowel, uterus or unknown masses, etc.; and
 h. for tissue confirmation of many non-malignant medical conditions.

I claim:

1. A biopsy needle, comprising:
 a one-piece body having a distal end defining a biopsy needle lumen, said distal end having a distal edge tissue cutting entrance of said one-piece body with a cross-sectional shape having a flat side extended transversely to a longitudinal axis of the biopsy needle and at least one converging side forming a shape selected from the group consisting of semicircular, elliptical, oval, rounded trapezoidal, paraboloid and triangular;
 a door disposed at said lumen, said door having a flat portion fitting said flat side of said distal edge tissue cutting entrance and at least one converging portion fitting said at least one converging side of said distal edge tissue cutting entrance;
 a hinge location of said one-piece body at said flat side of said distal edge tissue cutting entrance; and
 a hinge disposed at said hinge location;
 said door being moveable freely back and forth about said hinge, and said door being moveable about said hinge merely due to percutaneous insertion and percutaneous withdrawal of the needle, from a normally open position during percutaneous insertion, to a rotated and closed position totally occluding said lumen between said sides and said portions and automatically capturing a tissue biopsy specimen for removal.

2. The biopsy needle according to claim 1, wherein said door lies at least partially against said flat side in said normally open position, and contacts said converging side in said closed position.

3. The biopsy needle according to claim 1, wherein said door has a fixed portion with a forward edge tapered and sharpened to decrease tissue passage entrance resistance.

4. The biopsy needle according to claim 1, wherein said door has a door tip opposite said hinge location for contacting said converging side and occluding said lumen.

5. The biopsy needle according to claim 4, wherein said tip is tapered and sharpened on a side facing away from a distal end of said lumen and is turned down or angled toward a center of said lumen to catch and dig into the tissue biopsy specimen upon retraction of the biopsy needle.

6. The biopsy needle according to claim 1, wherein said distal end tissue entrance is angled other than 90° relative to said longitudinal axis of the biopsy needle.

7. The biopsy needle according to claim 1, wherein said hinge is an articulating hinge interconnecting said flat side and said door at said hinge location.

8. The biopsy needle according to claim 1, wherein said hinge is a tension-compression or live one-piece functional hinge interconnecting said flat side and said door at said hinge location.

9. The biopsy needle according to claim 1, wherein said hinge is a live or one-piece functional torsion element hinge interconnecting said flat side and said door at said hinge location.

10. The biopsy needle according to claim 1, wherein said door has at least one flexing area functioning as said hinge and formed by cutting into said door.

11. The biopsy needle according to claim 10, wherein said at least one flexing area is formed by a pattern of separation lines cut into said door.

12. The biopsy needle according to claim 10, wherein said door has a door tip opposite said hinge location defining a longitudinal direction of said door between said door tip and said hinge location, and said at least one flexing area is two flexing areas each extending perpendicularly to said longitudinal direction of said door.

13. The biopsy needle according to claim 12, wherein said door tip is angled into said lumen at one of said flexing areas closest to said door tip and is tapered and sharpened on a side facing away from a distal end of said lumen, to catch and dig into the tissue biopsy specimen upon retraction of the biopsy needle.

14. The biopsy needle according to claim 1, wherein said distal edge tissue entrance has a closed cross-sectional shape surrounding said lumen.

15. The biopsy needle according to claim 1, wherein said distal edge tissue entrance has a circumference and said flat side is disposed at said circumference.

* * * * *